United States Patent [19]

Hazar

[11] 4,019,253
[45] Apr. 26, 1977

[54] MEANS AND METHOD FOR PRODUCING CUSTOM ARTIFICIAL DENTURES

[75] Inventor: Mitchell M. Hazar, Phoenix, Ariz.

[73] Assignee: American Denture Corporation, Scottsdale, Ariz.

[22] Filed: Oct. 29, 1975

[21] Appl. No.: 626,851

[52] U.S. Cl. .................................................. 32/19
[51] Int. Cl.² ......................................... A61C 9/00
[58] Field of Search .................................. 32/19-21

[56] References Cited

UNITED STATES PATENTS

| | | | |
|---|---|---|---|
| 1,652,910 | 1/1926 | Psayla | 32/19 |
| 1,778,293 | 10/1930 | Galasso | 32/19 |
| 3,083,459 | 4/1963 | McMurry et al. | 32/2 |
| 3,464,111 | 9/1969 | Gillard | 32/2 |
| 3,465,440 | 9/1969 | Gareis | 32/2 |

Primary Examiner—G.E. McNeil

[57] ABSTRACT

A means and method for producing custom artificial dentures comprising a pair of trays adapted loosely to fit edentulus areas of a patient's mouth and stringers of generally U-shaped configuration having arrays of teeth afixed therein; the stringers being placed in the trays with the teeth projecting through the U-shaped openings therein, one tray for the maxillary and another tray for the mandibular area; a bite relator of deformable material engaged between the arrays of teeth held by said trays and impression forming material in the U-shaped recesses of the trays contiguous with the gums of a patient's mouth whereby impression castings may be made from which edentulus ridge fitting portions may be made and whereupon the respective stringers of teeth may then be bonded to the respective mandibulary and maxillary denture portions so formed.

10 Claims, 8 Drawing Figures

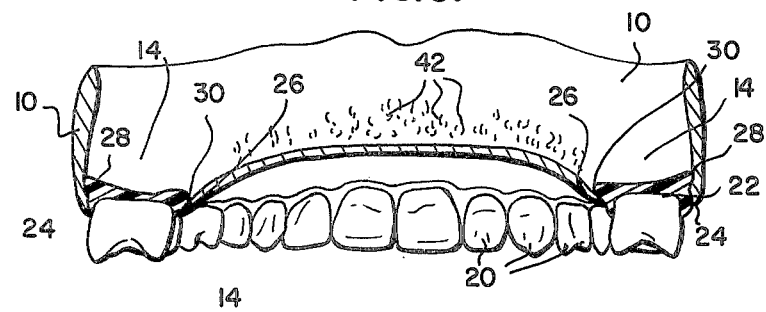
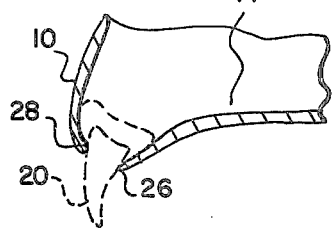
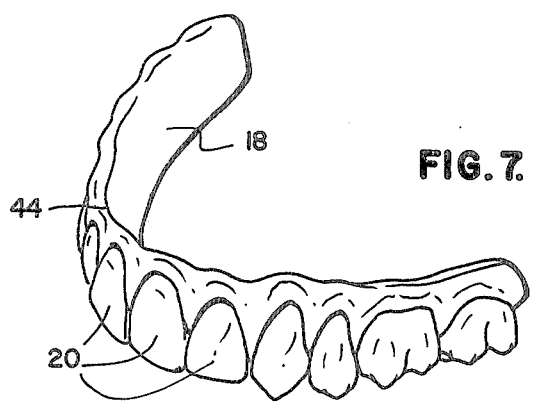
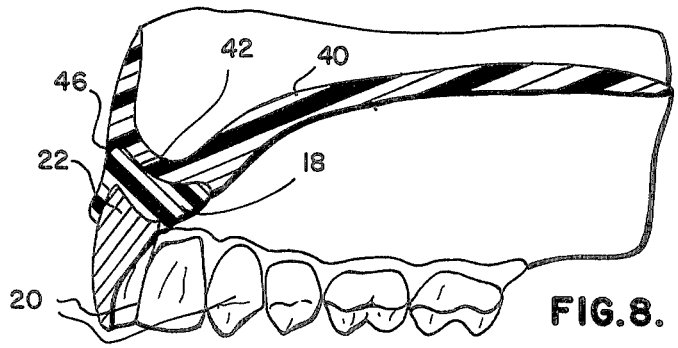

MEANS AND METHOD FOR PRODUCING CUSTOM ARTIFICIAL DENTURES

BACKGROUND OF THE INVENTION

Heretofore, custom artificial dentures have required a very time consuming and complicated method of producing dentures precisely in accordance with the features of a person's mouth to attain proper registry and relative occlusion between the maxillary and mandibulary artificial dentures. Heretofore, the conventional method of producing artificial dentures comprises complex wax-up setting of teeth and the taking of impressions as well as the usual process of obtaining proper registry between the maxillary and mandibulary dentures being produces. Additionally, problems of occlusion have also further complicated the usual process of producing custom dentures. Accordingly, custom dentures have been very expensive and time consuming on the part of the dentist and technician.

SUMMARY OF THE INVENTION

The present invention comprises a novel means and method for producing custom artificial dentures and particularly relative to a novel impression tray having a generally U-shaped recess in which a generally U-shaped opening receives an array of teeth bonded to a stringer which is held inside the tray and which is placed in a person's mouth with impression material between the stringer and an edentulus ridge so as to take an impression of the ridge and the stringer concurrently such that an edentulus ridge fitting denture portion may be produced from the impression and whereby the edentulus ridge fitting portion may then be bonded to the respective stringer which becomes a part of the custom denture. Further the invention comprises a novel method wherein a pair of the aforementioned trays are used with respective arrays of teeth from respective stringers projecting through the aforementioned U-shaped openings and wherein the respective teeth are engaged with a soft bite relator so as to hold the respective arrays of teeth in register and whereupon impression material is placed in the trays contiguous with the respective stringers and then the two trays are placed in a person's mouth into contact with both the maxillary and the mandibulary edentulus ridges therein for taking impressions which relate the respective stringers of teeth to the respective edentulus ridges whereupon the impressions may be used to produce edentulus ridge fitting denture portions which are then subsequently bonded to the respective stringers to thereby form dentures of which the stringers become an integral part.

Reference is hereby made to U.S. Pat. No. 3,464,111 issued to F. B. Gillard on Sept. 2, 1969. This patent discloses a method for self fitting dentures and discloses an alignment plate 20 which is used to provide registry of a pair of artificial dentures when impression fitted contiguous to the maxillary and mandibulary areas of a person's mouth. The present invention includes the use of the aforementioned alignment plate 20 when making impressions as aforementioned.

Accordingly, it is an object of the present invention to provide a novel impression tray for holding a stringer of teeth for taking an impression of an edentulus ridge area in a person's mouth.

Another object of the invention is to provide a novel stringer of artificial teeth for use in the aforementioned tray for taking an impression and for producing an edentulus ridge fitting denture portion which may later be bonded to the stringer of teeth which then become a permanent part of an artificial denture so produced.

Another object of the invention is to provide a novel method by which artificial dentures of a custom character may be produced very readily and simply and without the usual wax-up or the setting of teeth as has been common to the dental profession in the past.

Another object of the invention is to provide novel impression trays and stringers of artificial teeth all of which may be come in different sizes for fitting a great variety of patients.

Further objects and advantages of the invention may be apparent from the following specification, appended claims and accompanying drawings.

BRIEF DESCRIPTION OF THE DRAWINGS

FIG. 5 is an enlarged sectional view taken from the line 5—5 of FIG. 4;

FIG. 6 is an enlarged fragmentary sectional view taken from the line 6—6 of FIG. 3;

FIG. 7 is a perspective view of a stringer to which a generally U-shaped array of artificial dentures are bonded and contained in gum simulating material of the stringer; and FIG. 8 is a longitudinal sectional view of a maxillary artificial denture produced in accordance with the use of the trays and stringers and in accordance with the method of the invention.

DESCRIPTION OF THE PREFERRED EMBODIMENTS

Figure 1:
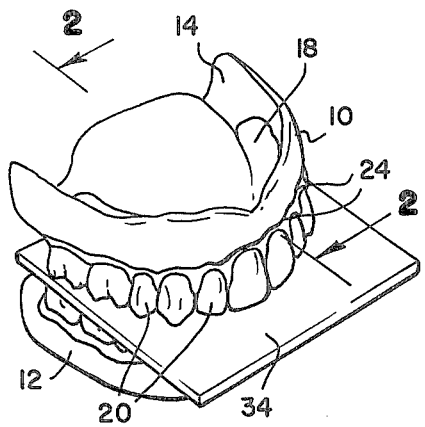
FIG. 1 is a perspective view of a pair of trays holding stringers of artificial teeth and coupled to a registery plate and adapted for insertion into contiguous relation with maxillary and mandibulary edentulus ridges of a patient's mouth.

As shown in FIGS. 1 to 4 of the drawings, the invention comprises maxillary and mandibular impression trays 10 and 12 respectively, the features of which are comparable and therefore the maxillary tray 10 will be described in detail.

As shown in FIG. 6 of the drawings, the maxillary tray 10 is provided with a generally U-shaped recessed portion 14 in which a generally U-shaped opening 16 is provided for receiving an array of teeth held by a stringer 18 as shown in FIG. 7 of the drawings. The stringer 18 is preferrably made of synthetic material such as a dental accrilic material and imbedded therein is a generally U-shaped array of artificial teeth designated 20. These artificial teeth as shown in FIGS. 5 and 8 are provided with root simulating portions 22 which are bonded in the substantially U-shaped stringer 18. Thus the stringer 18 carries the artificial teeth 20 and the generally U-shaped array of teeth 20 are extended through the opening 16 and the edges of the opening 16 are designated 24 and 26 in FIGS. 3 and 4 of the drawings. These edges 24 and 26 are irregular and conform to the contours of the sides of the teeth 20 on the stringer 18 and in FIG. 5 it will be seen that opposite edges 28 and 30 of the stringer 18 are spaced farther apart than the respective edges 24 and 26 of the opening 16 so that the stringer 18 will be retained in the respective tray 10 in the U-shaped recess 14 and thus align the teeth 20 to project beyond the respective edges 24 and 26 of the tray 10 and thus substantially enclosed the U-shaped opening 16 whereby suitable impression material may be placed in the respective trays 10 and 12 adjacent to the respective stringers 18. The impression material shown in FIG. 2 designated 32 may be conventional dental stone or other suitable impression material in soft uncured condition initially to be used in taking impressions of edentulus maxillary and mandibulary ridges of a patient's mouth. Additionally this material 32 also concurrently also makes an impression of the respective stringers 18. These stringers 18, being made of accrilic plastic material, are such that they simulate the color and configuration of human gums and ultimately become a part of the artificial denture to be produced.

Figure 2:
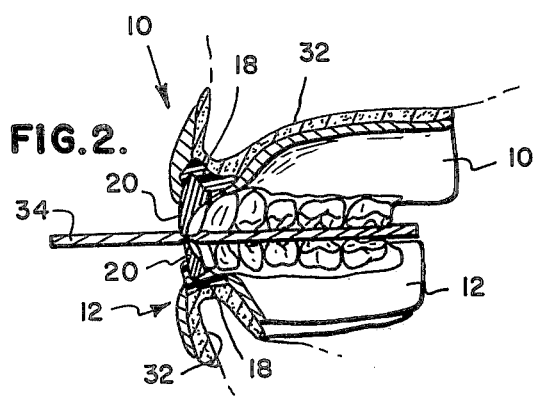
FIG. 2 is a sectional view taken from the line 2—2 of FIG. 1 but showing additionally the impression material in the trays and contiguous with the stringers.
Figure 3:
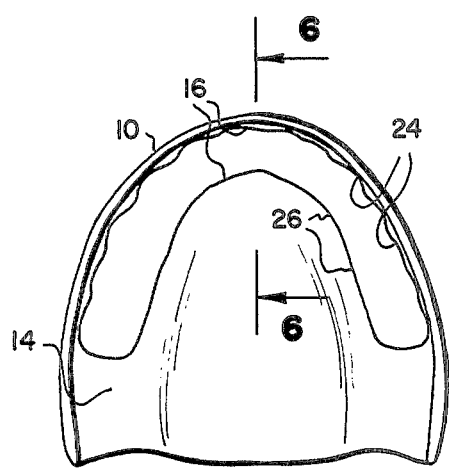
FIG. 3 is a planned view of a maxillary impression tray in accordance with the invention.
Figure 4:
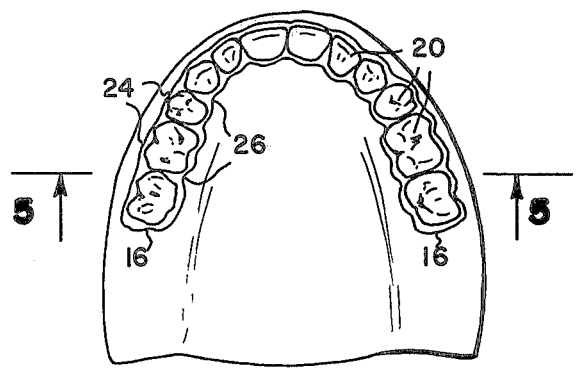
FIG. 4 is a view similar to FIG. 3 but showing an array of teeth held by a stringer and projected through a U-shaped opening in the tray as disclosed in FIG. 3.

As shown in FIGS. 1 and 2 of the drawings the teeth 20 projecting from the respective U-shaped openings of the trays 10 and 12 are engaged with a soft registery plate 34 in accordance with the disposition of the dentures to be worn in the patient's mouth. The entire assembly of the trays 10 and 12 with the respective stringers 18 and teeth 20 and the registery plate 34 together with the impression material 32 are placed in a person's mouth and impressions are taken of the maxillary and mandibulary edentulus ridges while at the same time taking related impressions of the respective upper and lower stringers 18 with their respective teeth; it being noted that the teeth 20 of the lowers are appropriate to the lower mandibulary area while the teeth 20 on the upper stringer 18 carried by the tray 10 are related to the usual maxillary denture configuration. The registery plate 34 maintains the respective stringers 18 together with the respective impression trays 10 and 12 in proper registery while the impression material sets up adjacent the edentulus ridges thereby making an impression of the ridges as well as the respective stringers 18 which ultimately become a part of the custom artificial denture being produced.

After the impressions are taken of the maxillary and mandibulary ridges in accordance with the disclosure of FIGS. 1 and 2, the impression material 32 in each of the trays 10 and 12 is removed and respective edentulus ridge fitting denture portions are reproduced according to the impressions 32 and are then bonded to the respective stringers 18 so as to complete the desired custom dentures. It will be understood that the stringers 18 while serving during the impression taking operation ultimately become a part of the denture such as shown in FIG. 8 wherein the edentulut ridge conforming denture part 40 is similar to the impression taken by the material 32 in the tray 10 and this part 40 is the part reproduced from the impression taken by the material 32 and the tray 10 and the edentulus ridge conforming part 40 is bonded at 42 to the respective stringer 18 with which the impression was taken. Accordingly, it will be appreciated that the part 40 when bonded to the respective stringer 18 is perfectly conforming to the patient's edentulus ridge while also maintaining a respective stringer which becomes a part of the denture in a proper registery with the mandibulary stringer and respective denture portion formed in accordance with the impression material 32 in the tray 12 as hereinbefore described.

It will be understood that the trays 10 and 12 will be available in various sizes to fit various patients and are generally arranged with a U-shaped recess 14 in which loosly conforms to the particular patient's mouth so as to permit the casting of the respective impression material 32 from which the conforming denture part 40 is modeled. Additionally, it will be understood that the stringers 18 together with the teeth 20 are provided in various sizes and configurations so as to match a great variety of patients and each stringer 18 matches its conforming U-shaped opening 16 in a respective tray as hereinbefore described. The stringers 18 are preferrably made of a flesh colored accrilic material and the trays such as the tray 10 are provided with festooning configuration 42 which will be disposed above a frontal portion 44 of the stringer 18 when in the respective tray so that the impression material 32 takes an impression of the festooning 42 and reproduces the festooning in the area 46 of the denture part 40, all as shown best in FIGS. 5, 7 and 8 of the drawings.

It will be obvious to those skilled in the art that various modifications may be resorted to without departing from the spirit of the invention.

I claim:
1. An impression tray for producing artificial dentures comprising: a tray member adapted generally to conform loosly with an edentulus ridge of a patient's mouth; said tray provided with a generally U-shaped recessed portion having a generally U-shaped opening in said U-shaped recessed portion adapted to hold a generally U-shaped stringer of artificial teeth such that said artificial teeth of said stringer project through said U-shaped opening.

2. The invention as defined in claim 1, wherein: said U-shaped opening is provided with irregularly formed edges surrounding it; said edges adapted to conform to the sides of the respective artificial teeth held by said stringer.

3. An impression tray for producing artificial dentures comprising: a tray member adapted generally to conform loosly with an edentulus ridge of a patient's mouth; said tray provided with a generally U-shaped recessed portion having a generally U-shaped opening in said U-shaped recessed portion; a generally U-shaped stringer carrying an array of artificial teeth; said teeth disposed in said U-shaped opening such that said artificial teeth of said stringer project through said U-shaped opening; said stringer having a cross sectional dimension greater than the lateral dimension of said U-shaped opening thereby retaining said stringer in said U-shaped recessed portion in said tray with said artificial teeth extending through said opening.

4. The invention as defined in claim 1, wherein: said tray member having upstanding side portions at opposite sides of said U-shaped recessed portion.

5. An impression tray for producing artificial dentures comprising: a tray member adapted generally to conform loosly with an endentulus ridge of a patient's mouth; said tray provided with a generally U-shaped recessed portion having a generally U-shaped opening in said U-shaped recessed portion; a generally U-shaped stringer carrying an array of artificial teeth; said teeth disposed in said U-shaped opening such that said artificial teeth of said stringer may project through said U-shaped opening; said U-shaped opening having irregularly formed edges; said edges adapted to conform to the sides of the respective artificial teeth held by said stringer; said stringer having a cross sectional dimension greater than the lateral dimension of said U-shaped opening thereby retaining said stringer in said U-shaped portion in said tray with said artificial teeth extending through said opening; said tray member having upstanding side portions at opposite sides of said U-shaped recessed portion, whereby impression material may be placed in said recessed portion between said upstanding sides and whereby said tray, stringer and impression material may be inserted in a person's mouth for concurrently taking a related impression of said edentulus ridge and said stringer.

6. An artificial tooth stringer of synthetic materials; said artificial tooth stringer having a generally U-shaped array of artificial teeth bonded therein; the shape of said stringer approximating the shape of a portion of the gum area adjacent a patient's teeth; said stringer being a relatively shallow structure compared to a complete artificial denture; said synthetic material generally surrounding root simulating portions of said teeth and being of a dimension greater than the side to side dimensions of said teeth.

7. A method for producing an artificial denture comprising: placing a U-shaped stringer of artificial teeth in a U-shaped tray with a U-shaped opening therein such that said teeth project through said opening; placing impression material in said tray contiguous to said stringer in said U-shaped tray; then placing the tray in a person's mouth with the impression material adjacent an edentulus ridge therein and concurrently taking a related impression of said stringer and said edentulus ridge; then using said impression material to produce an edentulus ridge fittng denture portion; then bonding said stringer of said artificial teeth to said respective ridge fitting denture portion.

8. A method of producing a related set of artificial dentures comprising: placing a pair of U-shaped stringers of artificial teeth in a pair of U-shaped trays, each having a U-shaped opening therein such that the teeth of each stringer project through a respective opening of a respective tray; placing impression material in said tray contiguous to said stringers in said U-shaped trays; then placing said trays in relative maxillary and mandibulary relation to each other with a deformable bite relator between the teeth on the respective stringers of said pair; then placing the trays in a person's mouth with the impression material against respective maxillary and mandibulary edentulus ridges therein and concurrently taking a related impression of said stringers and said edentulus ridges; then using said impression material to produce respective maxillary and mandibulary edentulus ridge fitting denture portions; then bonding said stringers of said artificial teeth to said respective maxillary and mandibulary ridge fitting portions.

9. The invention as defined in claim 1, wherein: said tray is provided with festooning mold features adjacent the area occupied by said stringer.

10. The invention as defined in claim 3, wherein: said tray is provided with festooning mold features adjacent the area occupied by said stringer.

* * * * *